United States Patent
Algawi et al.

(10) Patent No.: US 11,007,347 B2
(45) Date of Patent: May 18, 2021

(54) DEFLECTABLE INSERTION TOOL

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 253 days.

(21) Appl. No.: 15/867,114

(22) Filed: Jan. 10, 2018

(65) Prior Publication Data

US 2018/0311470 A1    Nov. 1, 2018

Related U.S. Application Data

(60) Provisional application No. 62/490,198, filed on Apr. 26, 2017.

(51) Int. Cl.
*A61M 25/01* (2006.01)
*A61B 17/24* (2006.01)
(Continued)

(52) U.S. Cl.
CPC ......... *A61M 25/0144* (2013.01); *A61B 17/24* (2013.01); *A61B 17/3421* (2013.01);
(Continued)

(58) Field of Classification Search
CPC ............... A61M 25/0147; A61M 25/0133
See application file for complete search history.

(56) References Cited

U.S. PATENT DOCUMENTS

| 5,772,578 A | 6/1998 | Heimberger et al. |
| 9,282,993 B1 | 3/2016 | Cohen et al. |

(Continued)

FOREIGN PATENT DOCUMENTS

| WO | 02/060352 A1 | 8/2002 |
| WO | 2009/152273 A1 | 12/2009 |

(Continued)

OTHER PUBLICATIONS

Extended European Search Report dated Sep. 13, 2018 for the European Patent Application No. 18169293.0.
(Continued)

*Primary Examiner* — Brandy S Lee
*Assistant Examiner* — Nidah M Hussain
(74) *Attorney, Agent, or Firm* — Volpe Koenig

(57) ABSTRACT

An insertion instrument is provided including a tube having a proximal end adapted to be gripped by a user and a distal end adapted for insertion. A tip control actuator is located at the proximal end, and the distal end of the tube includes a flexible portion. This flexible portion includes a spine and a plurality of circumferentially extending ribs extending from the spine. The ribs are axially spaced apart from a distal tip toward the proximal end, with the ribs being spaced apart by wedge shaped partial circumferential openings. The ribs have first and second axial sides defined by the wedge-shaped openings, with the first axial side of one of the ribs facing the second axial side of an adjacent one of the ribs. For each of the ribs, at least one of the first or second axial sides includes at least one of an axially extending projection or a recess and a facing one of the at least one of the first or second axial sides of an adjacent one of the ribs includes at least one of a complementary mating recess or a corresponding axial projection. At least one tension wire extends from the tip control actuator to the distal tip.

19 Claims, 10 Drawing Sheets

(51) Int. Cl.
*A61B 17/34* (2006.01)
*A61M 25/06* (2006.01)
*A61M 29/02* (2006.01)
*A61B 17/00* (2006.01)
*A61M 25/00* (2006.01)
*B23K 26/38* (2014.01)

(52) U.S. Cl.
CPC .... *A61M 25/0147* (2013.01); *A61M 25/0662* (2013.01); *A61M 29/02* (2013.01); *A61B 2017/00309* (2013.01); *A61B 2017/00318* (2013.01); *A61M 25/001* (2013.01); *A61M 25/0013* (2013.01); *A61M 2205/0216* (2013.01); *A61M 2210/0618* (2013.01); *B23K 26/38* (2013.01)

(56) References Cited

U.S. PATENT DOCUMENTS

| | | | |
|---|---|---|---|
| 10,188,413 B1 * | 1/2019 | Morriss | A61M 25/0147 |
| 2006/0004286 A1 | 1/2006 | Chang et al. | |
| 2006/0276775 A1 | 12/2006 | Rosenberg et al. | |
| 2008/0119693 A1 | 5/2008 | Makower et al. | |
| 2010/0023010 A1 | 1/2010 | Nelson et al. | |
| 2010/0193484 A1 | 8/2010 | Chen et al. | |
| 2011/0112365 A1 | 5/2011 | Galperin et al. | |
| 2011/0282379 A1 * | 11/2011 | Lee | A61F 2/01 606/200 |
| 2012/0078377 A1 | 3/2012 | Gonzales et al. | |
| 2012/0130381 A1 | 5/2012 | Germain | |
| 2016/0262754 A1 | 9/2016 | Altman | |
| 2016/0279386 A1 * | 9/2016 | Dale | A61M 25/0054 |
| 2016/0345947 A1 * | 12/2016 | Salahieh | A61B 17/00234 |
| 2017/0071688 A1 | 3/2017 | Cohen et al. | |

FOREIGN PATENT DOCUMENTS

| | | |
|---|---|---|
| WO | 2012/071464 A1 | 5/2012 |
| WO | 2016/142915 A1 | 9/2016 |
| WO | 2016/160694 A1 | 10/2016 |

OTHER PUBLICATIONS

Extended European Search Report dated Sep. 24, 2018 for the European Patent Application No. 18169302.9.

Extended European Search Report dated Apr. 22, 2020 for the European Patent Application No. 20156854.0.

* cited by examiner

DEFLECTABLE INSERTION TOOL

INCORPORATION BY REFERENCE

The following documents are incorporated herein by reference as if fully set forth: U.S. Provisional Patent Application No. 62/490,198, filed Apr. 26, 2017.

FIELD OF THE INVENTION

The present invention is related to insertion instruments, more specifically to medical insertion instruments, and in particular to an ENT tools for use in treatment of a paranasal sinus or other ear, nose, and throat applications.

BACKGROUND

Endoscopic sinus procedures, including surgery, are commonly used to treat chronic sinusitis. In many procedures, an endoscope is inserted into the nostril along with one or more surgical instruments. In certain procedures the insertion and subsequent withdrawal of a balloon into the tubular sinus passages is required. In other procedures, surgical instruments are inserted to cut and/or ablate tissue in order to improve drainage from the sinus cavity.

In order to reach access points of the various sinus cavities, ENT physicians typically use a tool set with multiple tools specifically adapted for insertion or guiding of instruments, each with a different angle, in order to allow the proper access to the desired site. The physician has to select the correctly angled tool or replace the tip of the tool with the correctly angled instrument, which can be cumbersome and involves additional costs.

It has been suggested to use a steerable or bendable tip for certain ENT tools. However, the flexible ends or tips of these known instruments do not remain rigid so that the physician can apply a force using the side or tip of the instrument, particularly when the tip is in the bent configuration.

It would be desirable to provide a reusable insertion instrument that is adjustably deflectable, but that can still remain rigid once it is bent or deflected so that a physician can apply pressure using the side or tip or the bent end section as necessary for various procedures.

SUMMARY

An insertion instrument is provided to address the issues with the prior known devices, and in a preferred application, is particularly suited for ENT procedures, such as the insertion of a balloon into a nasal cavity.

The insertion instrument comprises a tube having a proximal end adapted to be gripped by a user and a distal end adapted for insertion. A tip control actuator is located at the proximal end, and the distal end of the tube includes a flexible portion. This flexible portion includes a spine and a plurality of circumferentially extending ribs extending from the spine. The ribs are axially spaced apart from a distal tip toward the proximal end, with the ribs being spaced apart by wedge shaped partial circumferential openings. A widest part of the wedge-shaped openings is circumferentially opposite to the spine. The ribs have first and second axial sides defined by the wedge-shaped openings, with the first axial side of one of the ribs facing the second axial side of an adjacent one of the ribs. For each of the ribs, at least one of the first or second axial sides includes at least one of an axially extending projection or a recess and a facing one of the at least one of the first or second axial sides of an adjacent one of the ribs includes at least one of a complementary mating recess or a corresponding axial projection. At least one tension wire extends from the tip control actuator to the distal tip. This allows a user, by actuating the tip control actuator, to elastically bend/articulate the distal end of the tube to allow for insertion in a curved passage, such as a sinus cavity. At the same time, the projections enter or extend further into the recesses during bending of the distal end maintaining a rigid structure, allowing a sideways or normal force to be exerted by the tip as it is being inserted, which is often necessary in ENT procedures such as inserting a balloon, without the bent distal end of the tube shifting or collapsing. This interlocking arrangement of projections and recesses also provides a smooth inner surface that avoids tearing the balloon during manipulation and insertion.

In a preferred arrangement, the tip control actuator comprises a rotatable grip.

In a preferred arrangement, the tube comprises a guide tube connected to an end tube, with the end tube forming the distal end and including the flexible portion. This allows for the use of different materials for the tube, with each being optimized in terms of function and cost. Here, the end tube is formed of a superelastic material which allows for repeated use of the insertion instrument. In a preferred application, the end tube is made of Nitinol and has a wall thickness of about 0.4-0.6 mm, and a diameter of about 3.2-3.6 mm. However, other sizes and wall thicknesses can be used depending on the particular application.

In a preferred arrangement, the axially extending projections and corresponding complementary mating recesses and/or the recesses and the corresponding axial projections in the plurality of ribs are arranged in at least one axially extending row. Preferably, there are at least two rows of the axially extending projections and corresponding complementary mating recesses and/or the recesses and the corresponding axial projections. In one particularly preferred application, three of the axially extending rows of the axially extending projections and corresponding complementary mating recesses and/or the recesses and the corresponding axial projections are provided on the distal end, with a first one of the rows being located approximately 80-100 degrees from the spine, a second one of the rows being located approximately 170-190 degrees from the spine, and a third one of the rows being located approximately 260-280 degrees from the spine. The recesses and/or corresponding complementary mating recesses of the first and third rows have a curved path extending from the at least one of the first and second axial sides toward the spine, and the projections and/or corresponding axial projections of the first and third rows having a complementary curved shape to the curved path of the respective recesses or corresponding complementary mating recesses. The recesses and/or corresponding complementary mating recesses of the second row extend along a straight axial path and the respective projections or the corresponding axial projections have a complementary shape.

In a preferred arrangement, a clearance in a circumferential direction between axial projections and corresponding complementary mating recesses and/or the recesses and the corresponding axial projections is about 0.1-0.4 mm. This allows the bendable tip to be somewhat rigid to a sideways or normal force, even when bent due to bracing of the axial projections against the corresponding mating recesses and/or the corresponding axial projections against the recesses.

In a preferred arrangement, at least one opening is provided in the distal tip to connect the tension wire.

In a preferred arrangement, at least one of a complementary projection or a mating recess is located in the distal tip facing the first side of an adjacent one of the ribs. This allows for support and alignment of the distal tip with the distal-most rib.

In a preferred arrangement at least some of the axial projections are at least partially located in the corresponding complementary mating recesses or the corresponding axial projections are at least partially located in the recesses, or both, in an unbent state of the distal end of the tube. This allows for better support, guidance, and alignment of the ribs relative to one another during bending.

In a preferred arrangement, upon application of a tension force on the tension wire, the distal tip is deflectable from an unbent state in which the distal tip remains aligned with an axis of the insertion tool, to an intermediate state in which the distal tip is aligned at an angle to the axis and at least some spaces remain between at least some of the first and second axial sides of the ribs, to a fully deflected state in which the first and second axial sides of the ribs contact one another. Preferably, in each of the unbent state, the intermediate state, and the fully deflected state, at least some of the axial projections are circumferentially braced against sides of the corresponding complementary mating recesses and/or the corresponding axial projections are circumferentially braced against sides of the recesses to maintain a rigidity of the distal tip relative to a normally applied force.

In one preferred arrangement, the wedge-shaped openings all have a same shape. However, the shape of the wedge-shaped openings can be varied in order to achieve a variable bend profile. The bend profile can also be adjusted based on an axial width of the ribs.

In one preferred arrangement, at least one of a complementary projection or recess is provided in a part of the tube facing the second axial side of a proximal-most one of the ribs.

In one preferred arrangement, the tip control actuator includes the rotatable grip which has an internal thread, with the rotatable grip being axially fixed but rotatable on the tube. A sleeve with an external thread is provided, with the sleeve being slideable on the tube and the external thread engaging with the internal thread of the rotatable grip. The sleeve further includes an axially extending slot, and a projection connected to the tube extends into the slot to prevents rotation of the sleeve. The at least one tension wire is connected to the sleeve, and rotation of the rotatable grip causes an axial movement of the sleeve to apply tension on the distal tip via the tension wire in order to elastically bend the distal end.

In another aspect of the invention, a method of producing a bendable tip for an instrument, is provided, which includes: mounting a tube for an instrument in a CNC controlled rotational and axially movable holder of a laser cutting machine, with a distal end of the tube extending from the holder; activating a laser cutter; cutting wedge shaped partial circumferential openings in the tube to define a plurality of radially extending ribs at the distal end of the tube, with the ribs being connected together by an axially extending spine, and the ribs having first and second axial sides; during cutting, forming in each of the ribs in at least one of the first or second axial sides, at least one of an axial projection or a recess, and forming in a facing one of the at least one of the first or second axial sides of an adjacent one of the ribs at least one of a corresponding complementary mating recess or a corresponding axial projection.

In a preferred method, the holder is hollow, and tube stock that is cut to form the bendable tip can be axially advanced out of the holder and then cut to the desired tube length to form the tube, and a cutting process for the next bendable tip can then be carried out on the newly cut end of the tube stock.

In a further preferred aspect of the method, during cutting, at least one of a complementary projection or a mating recess is formed in an axial side of the distal tip that faces the first axial side of a first one of the ribs that is adjacent to the distal tip, with the at least one of the complementary projection or the mating recess being aligned with a corresponding one of the recess or the axial projection of a first one of the ribs that is adjacent to the distal tip.

In a further preferred aspect of the method, during cutting, at least one of a complementary projection or a mating recess is formed in an axial side of a part of the tube facing the second axial side of a last one of the ribs that is adjacent to a proximal part of the end tube, with the complementary projection or the mating recess being aligned with the at least one of the recess or the axial projection on the second axial side of the last one of the ribs.

In a further preferred aspect of the method, in order to form the insertion tool, a tension wire is connected to the distal end, and the tension wire extends through the tube to a tip control actuator located at a proximal end of the tube.

In a further preferred aspect of the method, during cutting, a clearance of about 0.1-0.4 mm is created in a circumferential direction between the axial projections and the corresponding complementary mating recesses and/or the recesses and the corresponding axial projections.

In a further preferred aspect of the method, the end tube is formed from a superelastic alloy, preferably Nitinol.

In a further preferred aspect of the method, after the laser cutting, at least one of electropolishing or abrasive cleaning of the tube is performed. Here electropolishing is preferred due to the enhanced smoothness of the surface finish obtained by this process and the ability to treat all surfaces.

In a further preferred aspect of the method, during cutting, at least one tension wire connection hole is formed at the distal end of the tube opposite to the spine.

In a further preferred aspect of the method, during cutting, rounded openings are formed at corners of the wedge shaped partial circumferential openings adjacent to the spine. Preferably, these rounded openings are oval and have a major axis extending in the axial direction of the tube.

As will be recognized by those of ordinary skill in the art from the present disclosure, the above-noted features can be utilized alone or in various combinations in order to provide enhanced functionality for insertion instruments.

BRIEF DESCRIPTION OF THE DRAWINGS

The foregoing Summary as well as the following Detailed Description will be best understood when read in conjunction with the appended drawings which show a preferred embodiment of the invention. In the drawings.

DETAILED DESCRIPTION OF THE PREFERRED EMBODIMENTS

Figure 1:
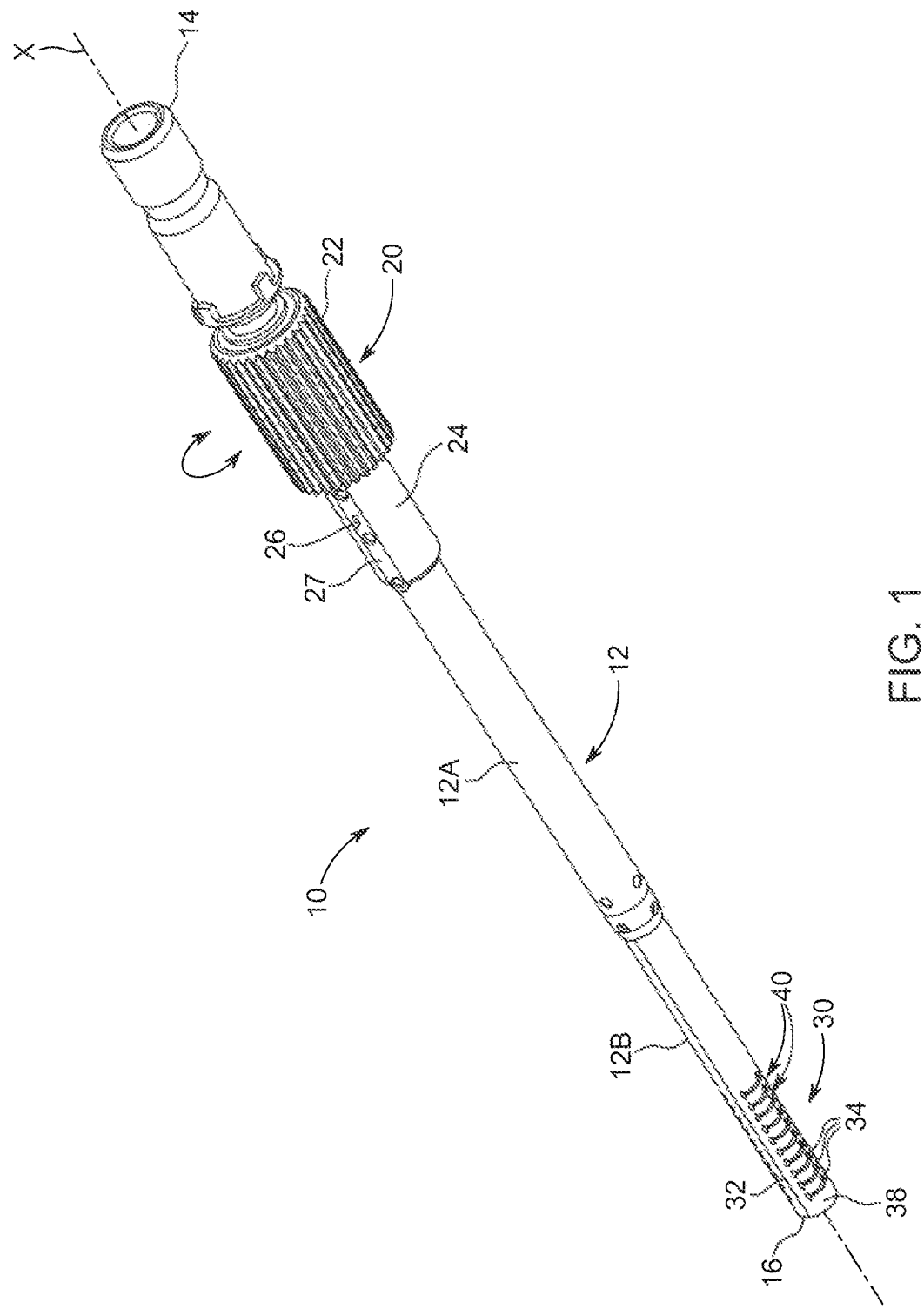
FIG. 1 is perspective view of an insertion instrument in accordance with an embodiment of the invention.
Figure 2:
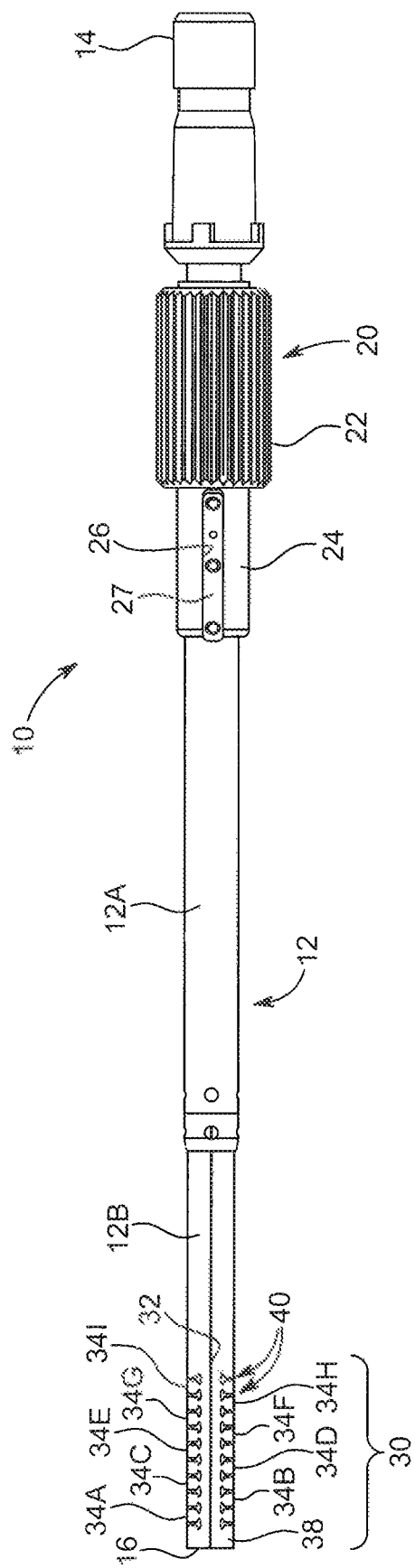
FIG. 2 is a top view of the insertion instrument shown in FIG. 1.
Figure 3:
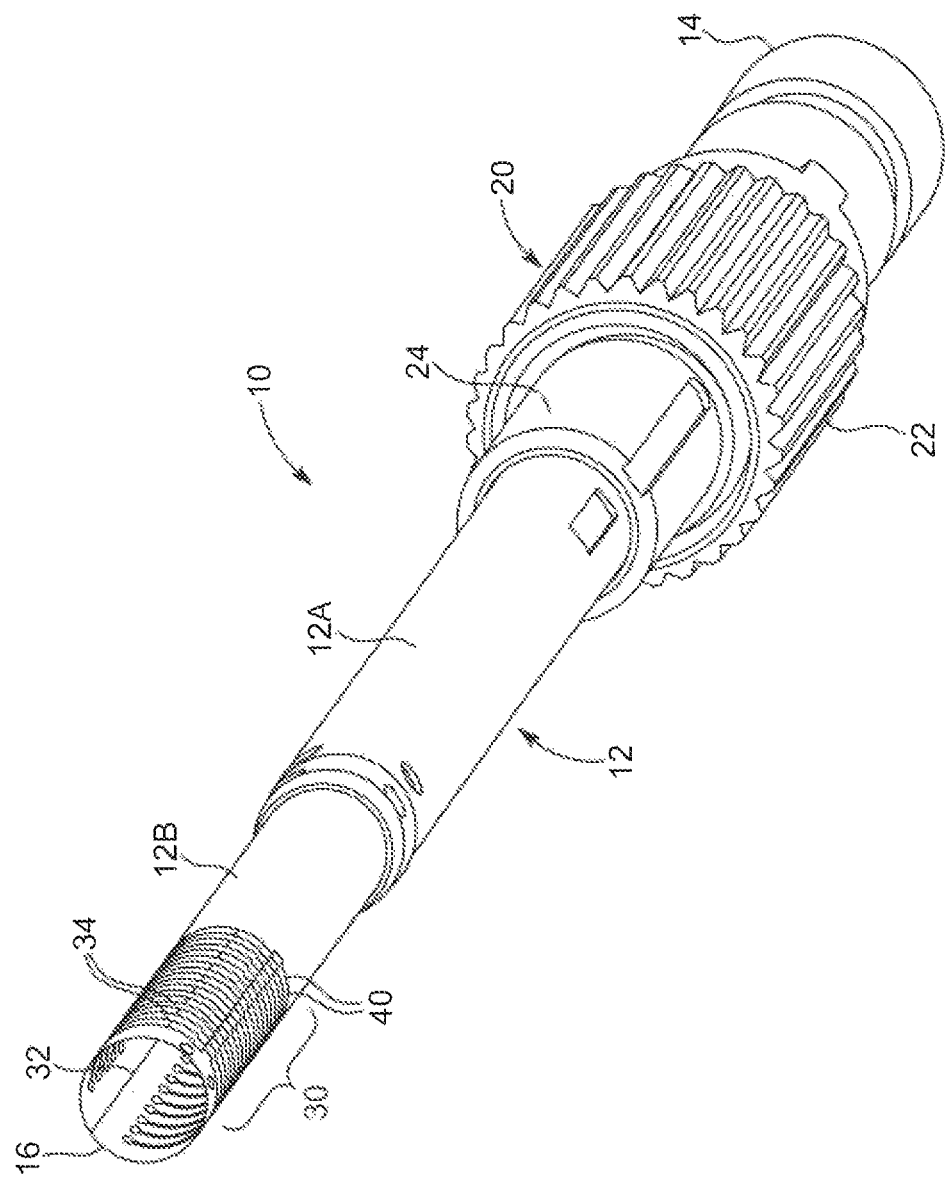
FIG. 3 is a bottom, front perspective view of the insertion instrument of FIG. 1.

Certain terminology is used in the following description for convenience only and is not limiting. The words "front," "rear," "upper" and "lower" designate directions in the drawings to which reference is made. The words "inwardly" and "outwardly" refer to directions toward and away from the parts referenced in the drawings. The terms "approximately" and "about" are intended to cover manufacturing tolerances associated with a particular dimension or range given. These terms and terms of similar import are for ease of description when referring to the drawings and should not be considered limiting. "Axially" refers to a direction along the axis of a shaft or similar object. A reference to a list of items that are cited as "at least one of a, b, or c" (where a, b, and c represent the items being listed) means any single one of the items a, b, or c, or combinations thereof. For the sake of convenience and clarity, the term "and/or" has been used in connection with description of the interfacing projections and recesses so that it is clear that the projections can be on either one of or both of two facing axial sides, and that the opposite one of or both of the two facing axial sides would include recesses in corresponding positions to the projections.

For elements of the invention that are identical or have identical actions, identical reference symbols are used. The illustrated embodiments represent merely examples for how the device according to the invention could be equipped. They do not represent a conclusive limitation of the invention.

Referring to FIGS. 1-4, an insertion instrument 10 is shown. The insertion instrument 10 includes a tube 12 having a proximal end 14 adapted to be gripped by a user and a distal end 16 adapted for insertion. The insertion instrument 10 is preferably for use in connection with ENT procedures, such as insertion of a balloon for expanding a sinus cavity. However, it can be used for various other medical or non-medical applications.

In the illustrated embodiment of the insertion instrument 10, the tube 12 is formed of a guide tube 12A located at the proximal end that is connected to an end tube 12B, located at the distal end. The end tube 12B includes a flexible portion 30.

As shown in FIGS. 1-4, a tip control actuator 20 is located at the proximal end 14. This tip control actuator 20 comprises a rotatable grip 22. However, other types of tip control actuators 20 could be utilized, such as an axially slideable grip.

Figure 4:
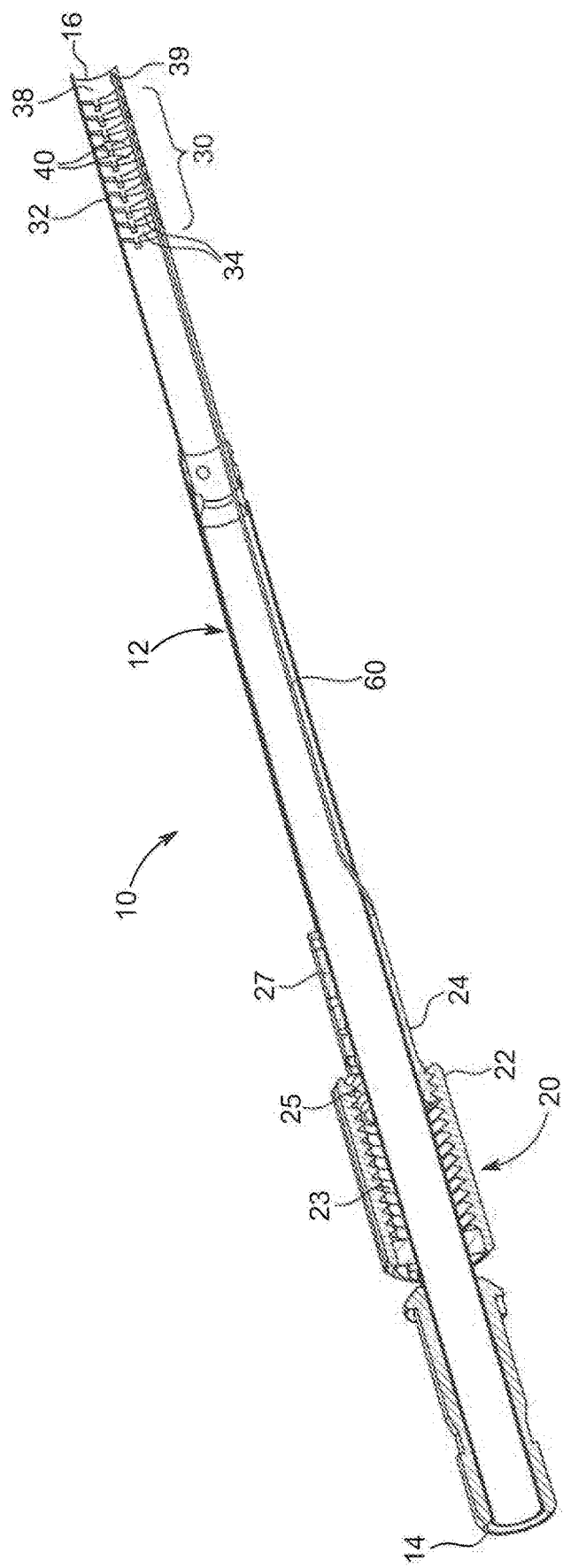
FIG. 4 is a longitudinal cross-sectional view through the insertion instrument of FIG. 1.

Referring to FIG. 4, in one preferred application, the rotatable grip 22 has an internal thread 23. The rotatable grip 22 is axially fixed but rotatable on the tube 12. A sleeve 24 with an external thread 25 is provided, with the sleeve 24 being slideable on the tube 12 in an axial direction and the external thread 25 of the sleeve 24 is engaged with the internal thread 23 of the rotatable grip 22. The sleeve 24 further includes an axially extending slot 26, and a projection 27 that is connected to the tube 12 extends into the slot 26 in order to prevent rotation of the sleeve 24 during turning of the rotatable grip 22. At least one tension wire 60, as discussed in further detail below, is connected to the sleeve 24. A further description of the function of tip control actuator 20 follows further below.

Still with reference to FIGS. 1-4 and with further reference to FIGS. 5-8, the flexible portion 30 at the distal end 16 of the tube 12 includes a spine 32 as well as a plurality of circumferentially extending ribs 34A-34I that extend from the spine 32 which are axially spaced apart from a distal tip 38 of the end tube 12B toward the proximal end. The ribs are generally referred to as 34, and the specific number of ribs 34A-34I could be varied depending upon the particular application for the insertion instrument 10 as well as the amount of bend required from the flexible portion 30. As shown in detail in FIGS. 5-8 and in further enlarged detail in FIG. 9, the ribs 34 are spaced apart by wedge-shaped partial circumferential openings 40. A widest part 42 of these wedge-shaped openings 40 is located circumferentially opposite to the spine 32.

Figure 9:
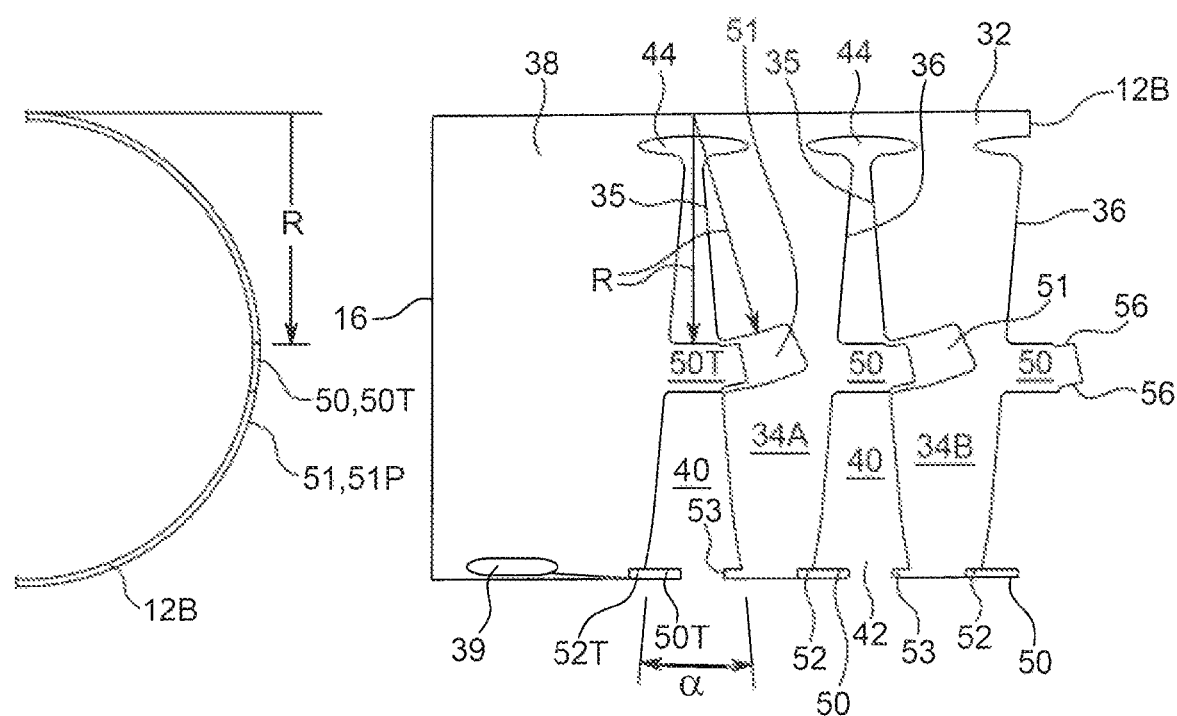
FIG. 9 is a greatly enlarged side elevational view of the distal tip of the insertion instrument of FIG. 1 along with a partial cross-sectional view.

The ribs 34 have first and second axial sides 35, 36, best shown in the enlarged detail of FIG. 9. These axial sides 35, 36 are defined by the wedge-shaped openings 40, with the first axial side 35 of one of the ribs, for example rib 34B, facing the second axial side 36 of an adjacent one of the ribs, for example rib 34A.

Figure 5:
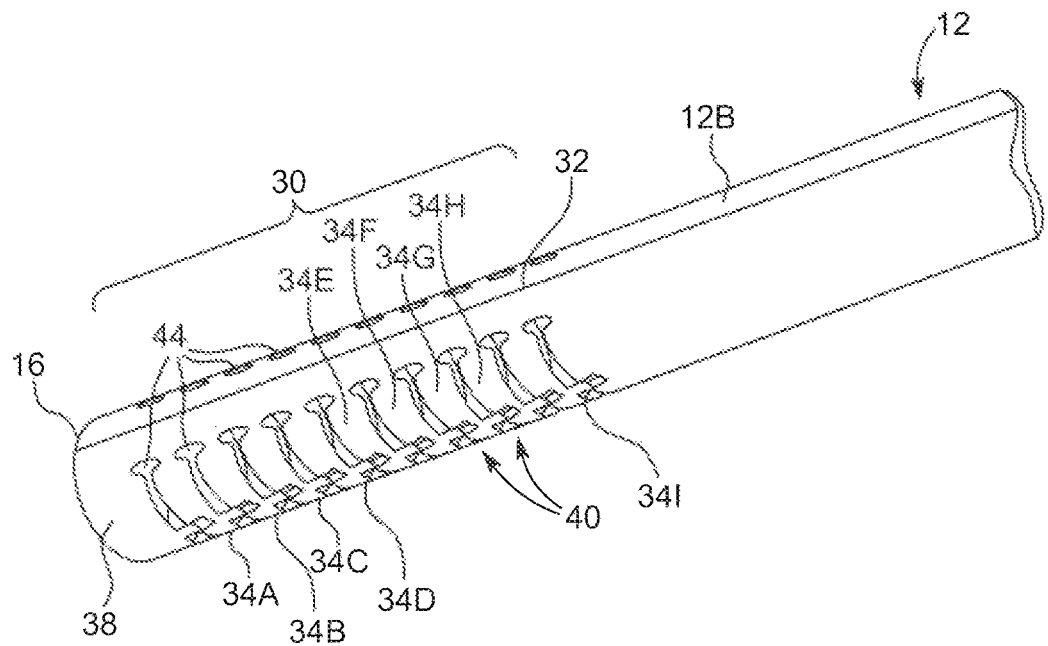
FIG. 5 is an enlarged perspective detail view of the distal end of the insertion instrument of FIG. 1.

As shown in detail in FIGS. 5 and 9, rounded openings 44 are provided at the corners of the wedge-shaped openings 40 adjacent to the spine 32. These rounded openings 44 are preferably oval, having a major axis extending in a direction of the axis X of the insertion instrument 10.

Still with reference to FIGS. 5-9, for each of the ribs 34, at least one of the first or second axial sides 35, 36 includes one of an axially extending projection 50 or a recess 52, and a facing one of the at least one of the first or second axial sides 35, 36 of an adjacent one of the ribs 34 includes at least one of a complementary mating recess 51 or a corresponding axial projection 53.

As shown in detail in FIGS. 5-9, it can be seen that the first rib 34A includes three of the axially extending projections 50 on the second axial side 36 and the facing first axial side 35 of an adjacent rib 34B includes three of the complementary mating recesses 51. Additionally, as can be seen most clearly in FIG. 8, the second axial side 36 of the first rib 34A includes a recess 52 and the first axial side 35 of the second rib 34B includes corresponding axial projections 53. While the illustrated embodiment includes both projections 20, 53 and recesses 51, 52 on both axial sides of the ribs 34, this is not required.

Figure 6:
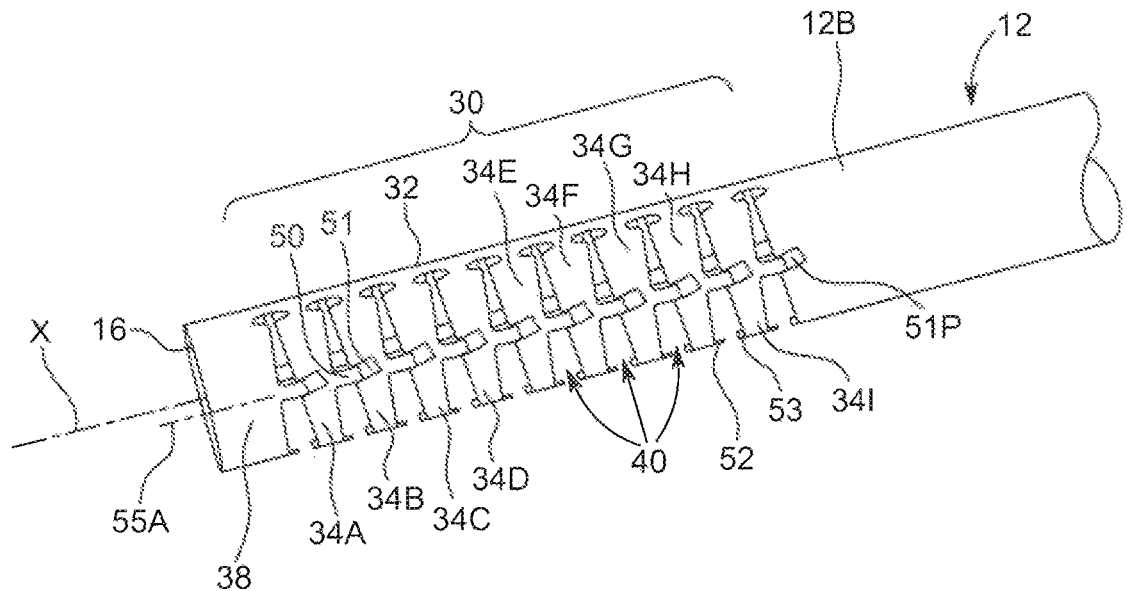
FIG. 6 is an enlarged elevational view of the distal tip of the insertion instrument of FIG. 1.
Figure 7:
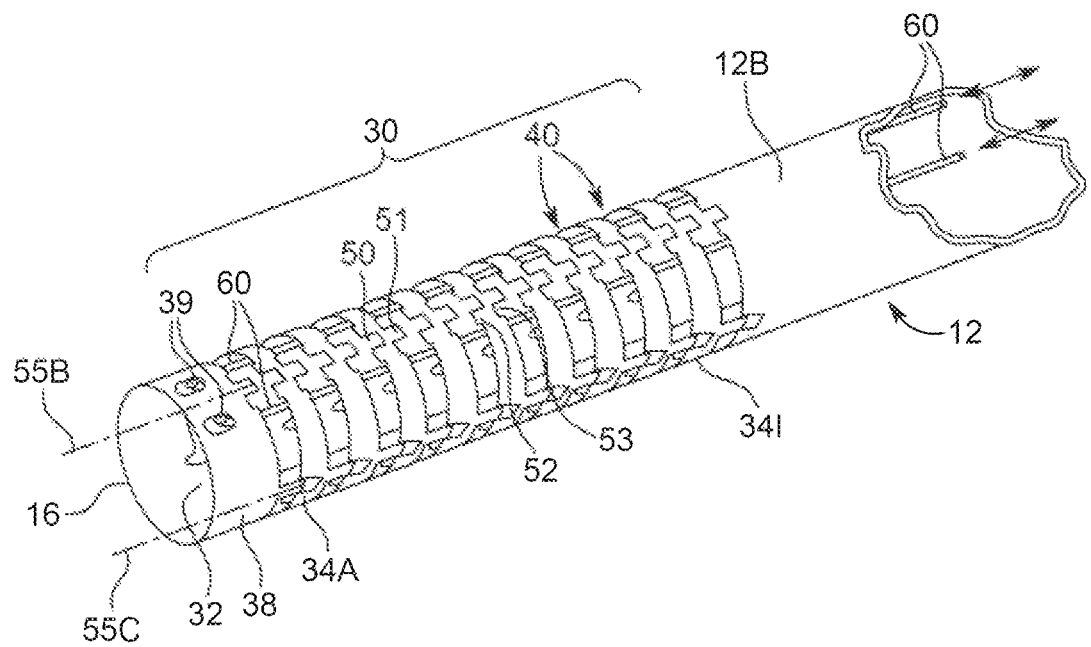
FIG. 7 is an enlarged bottom perspective view of the distal tip of the insertion instrument of FIG. 1.

In a preferred embodiment, the axially extending projections 50 and the corresponding complementary mating recesses 51 and/or the recesses 52 and the corresponding axial projections 53 in the plurality ribs 34A-34I are arranged in at least one axially extending low 55A, 55B, 55C, indicated in FIGS. 6 and 7. More preferably, there are at least two rows 55A-55C of the axially extending projections 50 and the corresponding complementary mating recesses 51 and/or the recesses 52 and the corresponding axial projections 53. In the illustrated embodiment, three of the axially extending rows 55A-55C of axially extending projections 50 and corresponding complementary mating recesses 51 and/or the recesses 52 and the corresponding axial projections 53 are provided. Here a first one of the rows 55A is located approximately 80°-100° from the spine 32. A second one of the rows 55B is located approximately 170°-190° from the spine 32. A third one of the rows 55C is preferably located approximately 260°-280° from the spine 32. The recesses 52 and/or the corresponding complementary mating recesses 51 of the first and third rows 55A and 55C, and in the illustrated embodiment only the complementary mating recesses 51, preferably have a curved path extending from the at least one of the first and second axial sides 35, 36 toward the spine 32. This curved path is shown in detail in FIG. 9 and preferably describes a radius R which generally corresponds to a bend radius of the tube end 12B at the location of the recesses 51 in the illustrated embodiment when it is being flexed. The projections, and in the illustrated embodiment only the axial projections 50, of the first and third rows 55A, 55C also have this complementary curved shape to the curved path of the corresponding complementary mating recesses 51.

Still with reference to FIG. 9, the axial projections 50 have a clearance in the circumferential direction of 0.1-0.4 mm with the complementary mating recesses 51. Similarly, the corresponding axial projections 53 have the same clearance with the recesses 52. In the area of the preferably curved path of the axial projections 50 and mating recesses 51, preferably the axial projections 50 have a reduced insertion area indicated at 56 where a width of the axial projection is made smaller to allow for easier guidance and insertion of the axial projection 50 as it enters the mating recess 51. In this area, the clearance can be greater than 0.4 mm. This also facilitated manufacturing.

Figure 8:
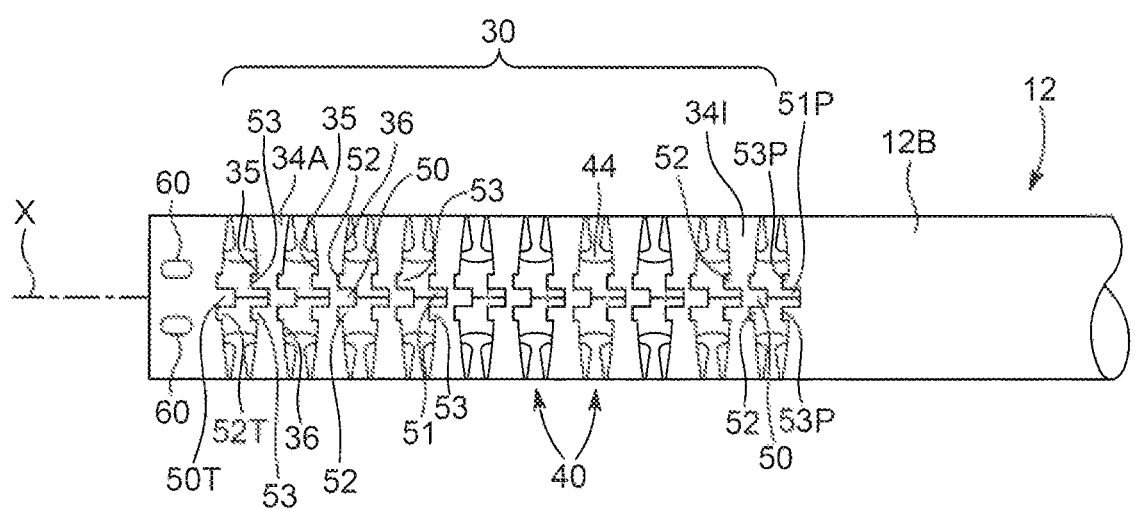
FIG. 8 is a bottom plan view of the distal tip of the insertion instrument of FIG. 1.

As shown in detail in FIG. 8, preferably the recesses 52 and/or the corresponding complementary mating recesses 51 of the second row 55b extend along a straight axial path, and the respective projections 50 or the corresponding axial projections 53 have a complementary shape.

While one preferred arrangement of the axial projections 50 and mating recesses 51 along with the recesses 52 and the corresponding axial projections 53 is shown, those skilled in the art will recognize that other configurations could be utilized and that these projections and recesses do not need to be arranged in rows as illustrated.

In the preferred arrangement, the end tube 12B is formed of superelastic material, such as Nitinol. Preferably, for us in ENT applications for insertion of a balloon catheter, the end tube 12B has a wall thickness of about 0.4-0.6 mm, and a diameter of 3.2-3.6 mm. Those skilled in the art will recognize that these dimensions can be changed for other applications and that other suitable materials may be utilized.

As shown in FIGS. 8 and 9, preferably at least one opening 39 is provided in the distal tip 38 to connect a tension wire 60. As shown in FIG. 4, at least one tension wire 60 extends from the tip control actuator 20 to the distal tip 38 where it is anchored in the at least one opening 39. In one preferred embodiment, two of the tension wires are provided in order to maintain a reduced cross-sectional diameter of the tension wires that projects into the clear open cross-section of the tube 12B while still carrying the necessary loads from the tip control actuator 20 to the distal tip 38 required for elastically bending the flexible portion 30 at the distal end 16 of the tube 12.

As shown in detail in FIGS. 5-9, at least one of a complementary projection 53T or a mating recess 51T is located in the distal tip 38 facing the first axil side 35 of an adjacent one of the ribs 34A. Further, as shown in detail in FIGS. 5-8, preferably at least one of a complementary projection 53P or recess 52P is provided in a part of the tube 12B facing the second axial side 36 of a proximal-most one of the ribs 34I. This is preferably provided in order to provide continuity in the ability to transfer normal forces against the flexible portion 30 of the distal end 16 of the tube 12 when it is in the flexed or bent position as discussed in further detail below.

Still with reference to FIGS. 5-9, preferably at least some of the axial projections 50 are at least partially located in the corresponding complementary mating recesses 51 and/or the corresponding axial projections 53 are at least partially located in the recesses 52 in an unbent state of the distal end 16 of the tube 12. This partial overlap ensures a smooth bending of the flexible portion 30 of the tube 12 when the tip control actuator 20 is actuated by a user.

Figure 10:
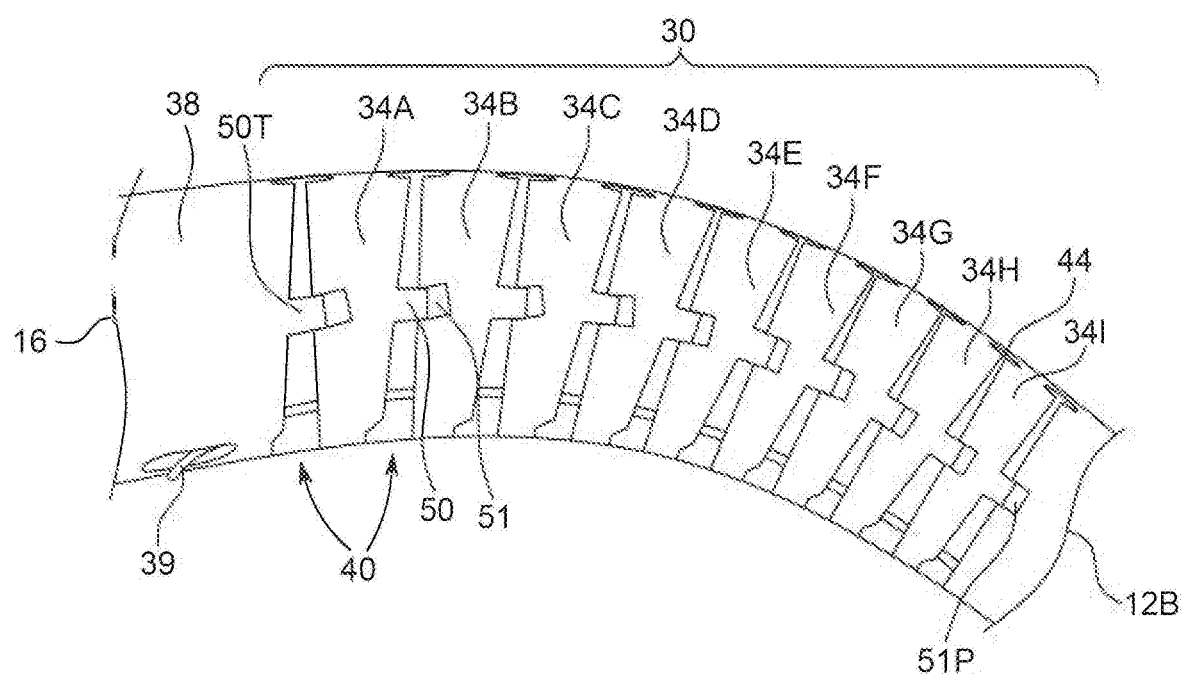
FIG. 10 is a side view showing the distal tip of the insertion instrument of FIG. 1 shown in a partially bent position.
Figure 11:
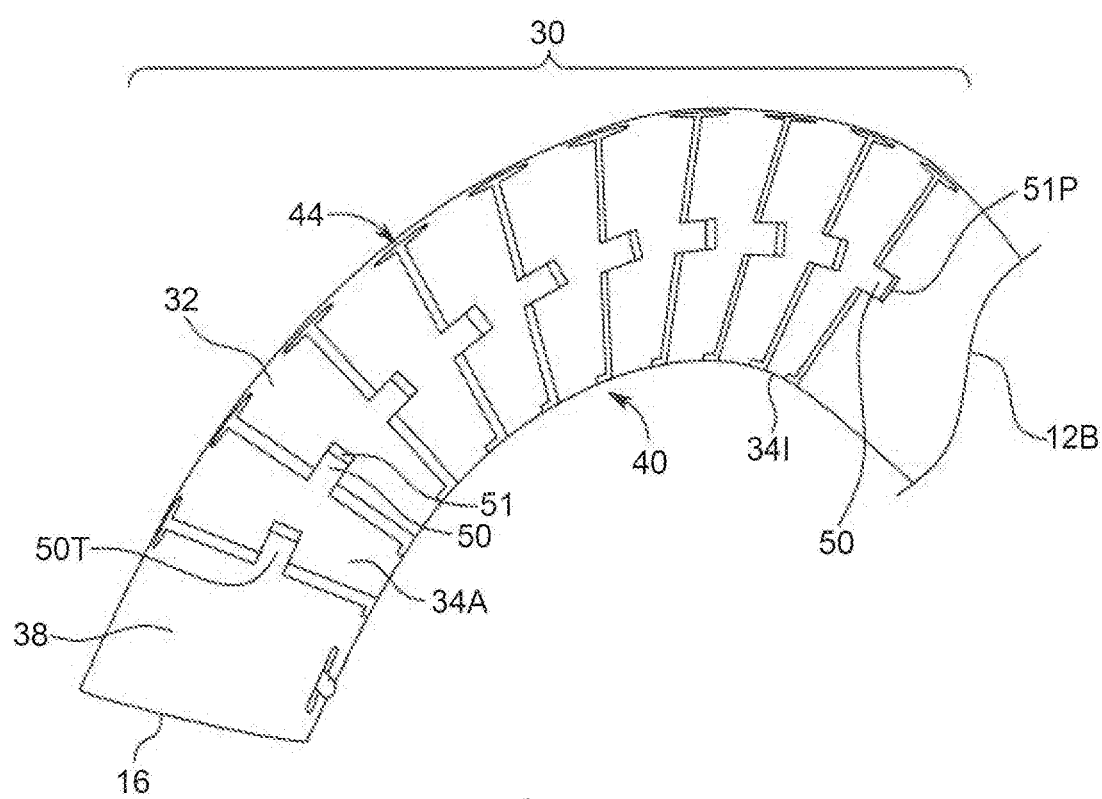
FIG. 11 is a side view of the distal tip of the insertion instrument of FIG. 10 shown in a further bent position.
Figure 12:
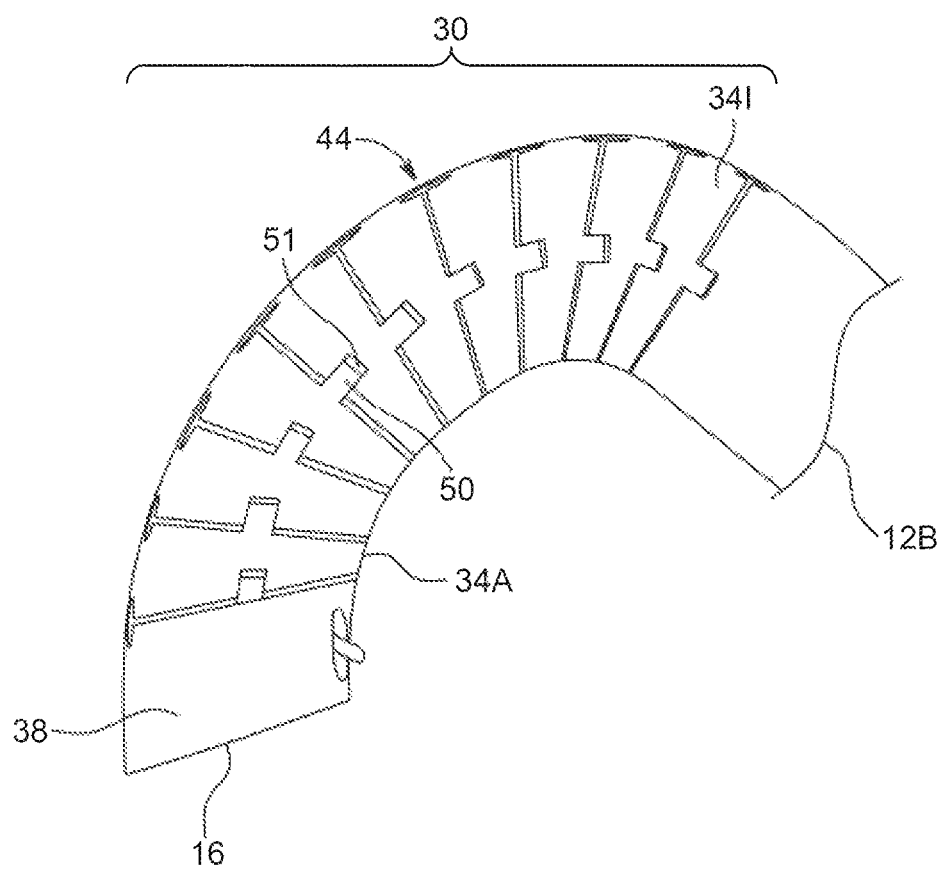
FIG. 12 is a side view of the insertion instrument of FIG. 10 shown in a fully bent configuration.

Referring to FIGS. 9-12, upon application of a tension force on the tension wire 60 using the tip control actuator 20, the distal tip 38 is deflectable from an unbent state in which the distal tip remains aligned with the axis X of the insertion tool 10, to one or more intermediate states as shown in FIGS. 10 and 11, in which the distal tip 38 is aligned at an angle to the axis X and at least some space remains between at least some of the first and second axial sides 35, 36 of the ribs 34, to a fully deflected state, as shown in FIG. 12, in which the first and second axial sides 35, 36 of the ribs 34 contact one another. In each of the intermediate state and the fully deflected state, at least some of the axial projections 50 are circumferentially braced against sides of corresponding complementary mating recesses 51 and/or the corresponding axial projections 53 are circumferentially braced against sides of the recesses 52 to maintain a rigidity of the distal tip 38 relative to a normally applied force on the distal tip 38. This is important for certain ENT applications where a normal force must be applied when the distal tip 38 is in the deflected position in order to push tissue out of the way as the insertion instrument 10 is advanced into a body cavity such as a sinus cavity.

In order to provide different bend profiles for the flexible portion 30, the wedge-shaped openings 40 may all have the same shape, as illustrated in detail in FIGS. 6 and 9. Alternatively, at least some of the wedge-shaped openings 40 may have different shapes to provide a variable bend profile. This can be done by varying the angle α indicated in FIG. 9 on some of the ribs at different locations. Alternatively, as is apparent from FIG. 10, some of the ribs 34 may have different widths which can also be used to adjust the bend profile.

In use, particularly for the embodiment of the insertion instrument 10 with the rotatable grip 22 that is shown in detail in FIGS. 1-4, in order to insert the insertion instrument 10 into a body cavity, such as a sinus cavity of a patient, the operator rotates the rotatable grip 22 in order to apply tension via the at least one tension wire 60 to the distal tip 38 such that the flexible portion 30 elastically bends into one or more of the intermediate or fully deflected states such as illustrated in FIGS. 10-12 in order to allow the operator to advance the insertion instrument 10 into the desired sinus cavity. Then, an instrument can be inserted through the tube 12, into the sinus cavity. This has particular application in connection with the insertion of a balloon catheter into a sinus cavity.

Figure 13:
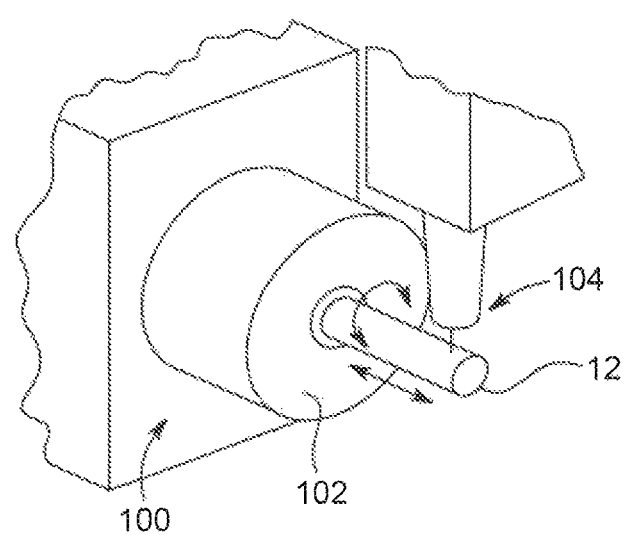
FIG. 13 is a perspective view of a CNC controlled laser cutting machine having a rotational and axially moveable holder.
Figure 14:
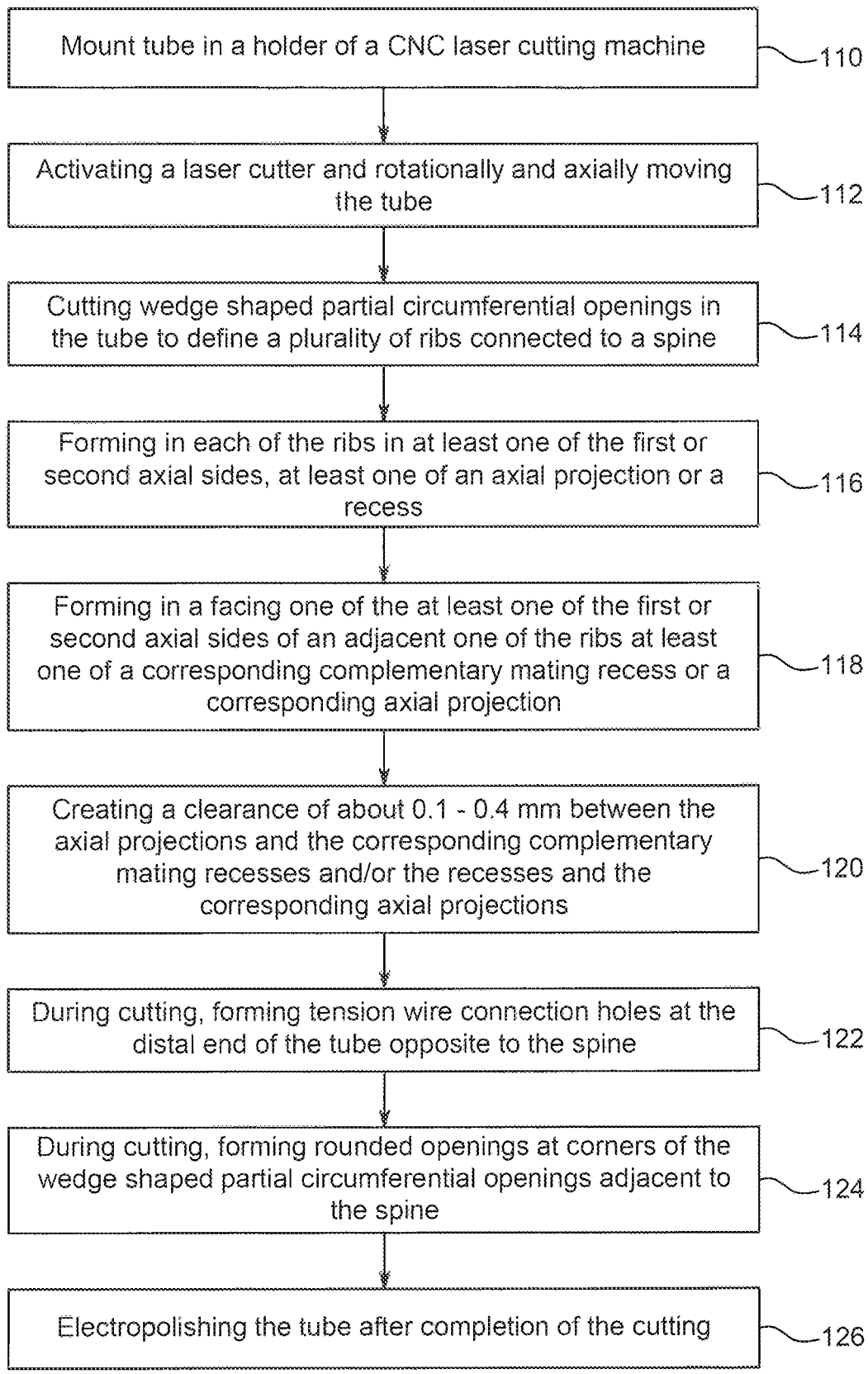
FIG. 14 is a flow chart showing a method for producing a bendable tip for an insertion instrument.

Referring now to FIGS. 13 and 14, a method for producing a bendable tip for an instrument 10 is also provided. The method includes mounting a tube 12 for the instrument in a CNC controlled rotational and axially moveable holder 102 of a laser cutting machine 100. This step is generally indicated at 110 in FIG. 14. One example of such a laser cutting machine is the Quantum-Cut Tube machine available from Blueacre Technology Ltd. of Louth, Ireland which provides a high accuracy four axis cutter that allows for cutting and profiling of tubes. Preferably, the moveable holder 102 includes a hollow chuck and long lengths of tube stock may be provided by inserting the tube stock through the chuck such that only a small portion of the tube is exposed for laser cutting. The laser 104, shown in FIG. 13, is then activated, as indicated in FIG. 14 at 112. The CNC controlled moveable holder then rotationally and axially moves the tube under the laser cutter in order to cut the wedge-shaped partial circumferential openings 40 (as shown in FIG. 9) in the tube 12 to define the plurality of ribs 34 which extend axially from the distal end of the tube 12. As discussed above, the ribs 34 are connected together by the axially extended spine 32. This is indicated at 114 in FIG. 14. During cutting, at least one of an axial projection 50 or a recess 52 is formed in each of the ribs in at least one of the first or second axial sides 35, 36. This is indicated at 116 in FIG. 14. Further, during cutting, at least one of a corresponding complementary mating recess 51 or a corresponding axial projection 53 is formed in a facing one of the at least one of the first or second axial sides 35, 36 of an adjacent one of the ribs 34. This is indicated at 118 in FIG. 14.

Preferably, during cutting, the complementary projections 53T or mating recesses 51T are formed in an axial side of the distal tip 38 that faces the first axial side 35 of a first one of the ribs 34A, and at least one of the complementary projections 53T or mating recesses 51T is aligned with a corresponding one of the recesses 52 or the axial projection 50 of the first one of the ribs 34A adjacent to the distal tip 38.

Further, during cutting at least one complementary projection 53P or a mating recess 51P is formed in an axial side of a part of the tube 12 facing the second axial side 36 of a last one of the ribs 341 that is adjacent to the proximal part of the tube 12. The complementary projection 53P or the mating recess 51P is aligned with the at least one of the recess 52 or the axially projection 50 on the second axial side 36 of the last one of the ribs 341.

During cutting of the axial projections and mating recesses, a clearance in the circumferential direction of about 0.1-0.4 mm is provided in order to provide for smooth bending operation of the flexible portion 30 while still allowing the bracing contact between the respective projections and the recesses so that a normal force can be applied to the distal end 38 in use without the flexible portion 30 at the distal end 16 of the tube 12 collapsing or flexing. This is indicated at 120 in FIG. 14.

Preferably, during cutting, a tension wire connection opening 39 is formed at the distal end 16 of the tube circumferentially opposite to the spine 32. This allows connection of the tension wire 60 to the distal tip 38 in a later step. This is indicated at 122 in FIG. 14.

Preferably, during cutting, rounded openings 44 are formed at the corners of the wedged-shaped partial circumferential openings 40 adjacent to the spine 32. This is indicated at 124 in FIG. 14.

Once the cutting of the tube 12 is completed, to the extent that this is only a portion of a longer piece of tube stock from which multiple such tubes 12 can be formed, the tube stock is advanced through the moveable holder 102 until a sufficient length is exposed to form the desired length for the tube 12 and the completed tube 12 is cut from the end of the tube stock. At that point the next cutting operating for forming the next tube 12 can be initiated.

Once cutting of the tube 12 has been completed, it is preferably at least one of electropolished or abrasively cleaned in order to remove any sharp edges and smooth over any imperfections in the areas of the laser cutting. Electropolishing is preferred due to the smooth surface finish provided which does not include any abrasive scratch lines due to the electropolishing process used. Alternatively, depending on the particular application for the instrument 10, an abrasive cleaning, for example, in a shaker with an abrasive media could also be utilized.

Once the tube 12 is complete, or if the only portion formed using laser cutting is the end tube 12B, this can be assembled with the guide tube 12A to complete the tube 12, and then the tip control actuator 20 can be assembled to the tube 12. The at least one tension wire 60 is then connected from the at least one connection opening 39 and extended through the tube 12 for connection to the tip control actuator 20.

The insertion instrument 10 then provides the advantage of not requiring separate tips having different bend angles since the construction of the flexible portion 30 is specifically designed to allow for the application of a normal force without the distal tip 38 being unduly deflected in a manner that would hinder the insertion process, particularly in ENT applications.

Having thus described the present invention in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

The invention claimed is:

1. An insertion instrument, comprising:
 a tube having a proximal end, and a distal end adapted for insertion;
 a tip control actuator located at the proximal end;
 the distal end of the tube including a flexible portion and comprising
 a spine,
 a plurality of circumferentially extending ribs extending from the spine and being axially spaced apart from a distal tip toward the proximal end, the ribs being spaced apart by wedge shaped partial circumferential openings,
 the ribs have first and second axial sides defined by the wedge-shaped openings, with the first axial side of one of the ribs facing the second axial side of an adjacent one of the ribs, for each of the ribs, at least one of the first or second axial sides including at least one of an axially extending projection or a recess and facing one of the at least one of the first or second axial sides of an adjacent one of the ribs including at least one of a complementary mating recess or a corresponding axial projection, wherein at least one of the recesses and/or complementary mating recesses in the plurality of ribs includes a curved path, and at least one of the axially extending projections and/or corresponding axial projections in the plurality of ribs includes a curved shape complementary to the curved path, wherein said curved path and said curved shape approximate a bend radius of the flexible portion of the tube when flexed;

at least one tension wire extending from the tip control actuator to the distal tip wherein upon application of a tension force on the tension wire, the distal tip being deflectable from an unbent state in which the distal tip remains aligned with an axis of the insertion instrument, to an intermediate state in which the distal tip is aligned at an angle to the axis and at least some spaces remain between at least some of the first and second axial sides of the ribs, to a fully deflected state in which the first and second axial sides of the ribs contact one another; and wherein in each of the intermediate state and the fully deflected state, at least some of the axial projections are circumferentially braced against sides of the corresponding complementary mating recesses and/or the corresponding axial projections are circumferentially braced against sides of the recesses to maintain a rigidity of the distal tip relative to a normally applied force on the distal tip.

2. The insertion instrument of claim 1, wherein the tip control actuator comprises a rotatable grip.

3. The insertion instrument of claim 1, wherein the tube comprises a guide tube connected to an end tube, with the end tube forming the distal end of the tube and including the flexible portion.

4. The insertion instrument of claim 3, wherein the end tube is formed of a super elastic material.

5. The insertion instrument of claim 1, wherein the end tube is made of Nitinol and has a wall thickness of about 0.4-0.6 mm, and a diameter of about 3.2-3.6 mm.

6. The insertion instrument of claim 1, wherein the axially extending projections and corresponding complementary mating recesses and/or the recesses and the corresponding axial projections in the plurality of ribs are arranged in at least one axially extending row.

7. The insertion instrument of claim 6, wherein there are at least two rows of the axially extending projections and corresponding complementary mating recesses and/or the recesses and the corresponding axial projections.

8. The insertion instrument of claim 6, wherein there are three of the axially extending rows of the axially extending projections and corresponding complementary mating recesses and/or the recesses and the corresponding axial projections on the distal end of the tube, with a first one of the rows being located approximately 80-100 degrees from the spine, a second one of the rows being located approximately 170-190 degrees from the spine, and a third one of the rows being located approximately 260-280 degrees from the spine.

9. The insertion instrument of claim 8, wherein the recesses and/or corresponding complementary mating recesses of the second row extend along a straight axial path and the respective projections or the corresponding axial projections have a complementary shape.

10. The insertion instrument of claim 1, wherein a clearance in a circumferential direction between axial projections and corresponding complementary mating recesses and/or the recesses and the corresponding axial projections is 0.1-0.4 mm.

11. The insertion instrument of claim 1, further comprising at least one opening in the distal tip to connect the tension wire.

12. The insertion instrument of claim 1, further comprising at least one of a complementary projection or a mating recess located in the distal tip facing the first axial side of an adjacent one of the ribs.

13. The insertion instrument of claim 1, wherein at least some of the axial projections are at least partially located in the corresponding complementary mating recesses or the corresponding axial projections are at least partially located in the recesses, or both, in an unbent state of the distal end of the tube.

14. The insertion instrument of claim 1, wherein a widest part of the wedge-shaped openings is located circumferentially opposite to the spine.

15. The insertion instrument of claim 1, wherein at least some of the wedge-shaped openings have different shapes to provide a variable bend profile.

16. The insertion instrument of claim 1, further comprising at least one of a complementary projection or recess in a part of the tube facing the second axial side of a proximal-most one of the ribs.

17. The insertion instrument of claim 1, wherein the tip control actuator comprises a rotatable grip having an internal thread, the rotatable grip being axially fixed but rotatable on the tube, a sleeve with an external thread, the sleeve is slideable on the tube and the external thread is engaged with the internal thread of the rotatable grip, the sleeve further including an axially extending slot, and a projection connected to the tube that extends into the slot that prevents rotation of the sleeve, and the at least one tension wire is connected to the sleeve.

18. The insertion instrument of claim 1, wherein at least some of the ribs have different axial widths.

19. The insertion instrument of claim 1, wherein in each of the intermediate state and the fully deflected state, at least some of the axial projections are circumferentially braced against sides of the corresponding complementary mating recesses and the corresponding axial projections are circumferentially braced against sides of the recesses to maintain a rigidity of the distal tip relative to a normally applied force on the distal tip.

* * * * *

UNITED STATES PATENT AND TRADEMARK OFFICE
CERTIFICATE OF CORRECTION

PATENT NO. : 11,007,347 B2
APPLICATION NO. : 15/867114
DATED : May 18, 2021
INVENTOR(S) : Yehuda Algawi et al.

It is certified that error appears in the above-identified patent and that said Letters Patent is hereby corrected as shown below:

In the Specification
In Column 4, Line 56, delete "FIG. 1 is" and insert -- FIG. 1 is a --, therefor.
In Column 6, Lines 59-60, delete "projections 20, 53" and insert -- projections 50, 53 --, therefor.
In Column 9, Line 56, delete "distal end 38" and insert -- distal end 16 --, therefor.

Signed and Sealed this
First Day of November, 2022

Katherine Kelly Vidal
*Director of the United States Patent and Trademark Office*